United States Patent [19]

Oki et al.

[11] 4,386,198

[45] May 31, 1983

[54] 2-HYDROXYACLACINOMYCIN A AND 2-HYDROXYAKLAVINONE AND PROCESS FOR PREPARING SAME

[75] Inventors: Toshikazu Oki, Yokohama; Akihiro Yoshimoto, Fujisawa; Kageaki Kouno, Tokyo; Taiji Inui, Yatsushiro; Tomio Takeuchi; Hamao Umezawa, both of Tokyo, all of Japan

[73] Assignee: Sanraku-Ocean Co., Ltd., Tokyo, Japan

[21] Appl. No.: 184,518

[22] Filed: Sep. 5, 1980

[30] Foreign Application Priority Data

Sep. 7, 1979 [JP] Japan .................................. 54-115520
Jul. 7, 1980 [JP] Japan .................................. 55-92880

[51] Int. Cl.³ .................... C07H 15/24; A61K 31/71; C12P 19/56

[52] U.S. Cl. .................................. 536/6.4; 424/180; 424/181; 435/78; 260/365

[58] Field of Search ...................... 260/365; 536/17 A

[56] References Cited

U.S. PATENT DOCUMENTS

| 3,988,315 | 10/1976 | Umezawa et al. | 536/17 A |
| 4,020,270 | 4/1977 | Arcamone et al. | 536/17 A |
| 4,144,329 | 3/1979 | Umezawa et al. | 536/17 A |

*Primary Examiner*—Johnnie R. Brown
*Attorney, Agent, or Firm*—Jordan and Hamburg

[57] ABSTRACT

New anthracycline compounds, 2-hydroxyaclacinomycin A having potent antitumor activity and lower toxicity, 2-hydroxyaklavinone as an useful precursor for producing anthracycline glycosides, and a process for the production thereof by microbial conversion method are disclosed.

3 Claims, 2 Drawing Figures

FIG. I

2-HYDROXYACLACINOMYCIN A AND 2-HYDROXYAKLAVINONE AND PROCESS FOR PREPARING SAME

BACKGROUND OF THE INVENTION (1) Field of the Invention

The present invention relates to novel anthracycline compounds and a process for the production thereof. More particularly, the present invention relates to novel anthracycline compounds of the general formula I:

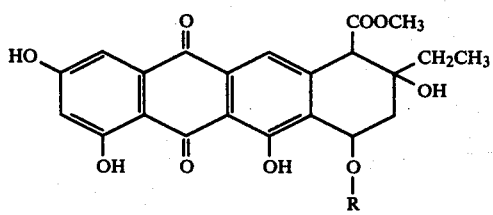

wherein R represents a hydrogen atom or the following sugar chain: rhodosamine-2-deoxyfucose-cinerulose residue

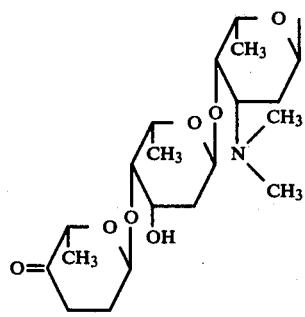

and to a process for the production thereof.

(2) Description of the Prior Art

A number of anthracycline glycosides have been found in the culture medium of Streptomyces, and are described in prior literature. Among them, daunomycin and adriamycin have already been clinically applied for human cancers.

Rhodomycinones, iso-rhodomycinone and rhodomycin-related antibiotics are described in Chem. Ber. 88, 1792–1818 (1955); Chem. Ber. 101, 1341–1348 (1968); J. Med. Chem., 20, 957–960 (1977); Pharmacie 27, 782–789 (1972); Zeit. Allg. Mikrobiol., 14, 551–558 (1974); Tetrahed. Lett. No. 38, 3699–3702 (1973); Folia Microbiol., 24, 293–295 (1979); and J. Antibiotics, 32, 420 (1979).

Aclacinomycin A is disclosed in U.S. Pat. No. 3,988,315 and by Oki et al. in J. Antibiotics 28, 830 (1975) and 32, 791–812 (1979).

Cinerubins A and B are disclosed in U.K. Pat. No. 846,130, U.S. Pat. No. 3,864,480, Keller-Schierlein et al., "Antimicrobial Agents and Chemotherapy", page 68 (1970), Chemical Abstracts 54, 1466i (1960) and J. Antibiotics 28, 830 (1975).

Further illustrative and summary disclosures of anthracycline antibiotics can be located in Index of Antibiotics from Actinomycetes, Hamao Umezawa, Editor-in-Chief, University Park Press, State college, Pennsylvania, U.S.A. (1967) as follows:

| Antibiotics | Page numbers |
|---|---|
| Aclacinomycins A and B | 101–102 |
| Adriamycin | 122 |
| Carminomycin I | 225 |
| Galirubins S–D | 405–408 |
| Rhodomycins X–Y | 879–880 |
| β-Rhodomycins | 881–885 |
| γ-Rhodomycins | 886–892 |
| Steffimycin | 945 |

The textbook, Antibiotics, Volume 1, Mechanisms of Action, edited by David Gottlieb and Paul D. Shaw, Springer-Verlag New York, Inc., N.Y. (1967) at pages 190–210 contains a review by A. DiMarco entitled "Daunomycin and Related Antibiotics".

Information Bulletin, No. 10, International Center of Information of Antibiotics, in collaboration with WHO, December, 1972, Belgium, reviews anthracyclines and their derivatives.

SUMMARY OF THE INVENTION

The novel anthracycline compounds according to the present invention include 2-hydroxyaclacinomycin A and the non-toxic acid addition salt thereof and 2-hydroxyaklavinone.

Other embodiments of the present invention provide a new process for producing 2-hydroxyaclacinomycin A by cultivating a microorganism of streptomyces capable of converting anthracyclinone to anthracycline glycoside and adding 2-hydroxyaklavinone to the cultured medium of said microorganism during cultivation to produce and isolate said antibiotic from the cultured medium.

Still other embodiments of the present invention provide a pharmaceutical containing sufficient amount of said antibiotic of the present invention or a non-toxic acid addition salt thereof to inhibit the growth and nucleic acid biosynthesis of malignant tumors such as L 1210 leukemia in mammals.

DETAILED DESCRIPTION OF THE INVENTION

Figure 1:
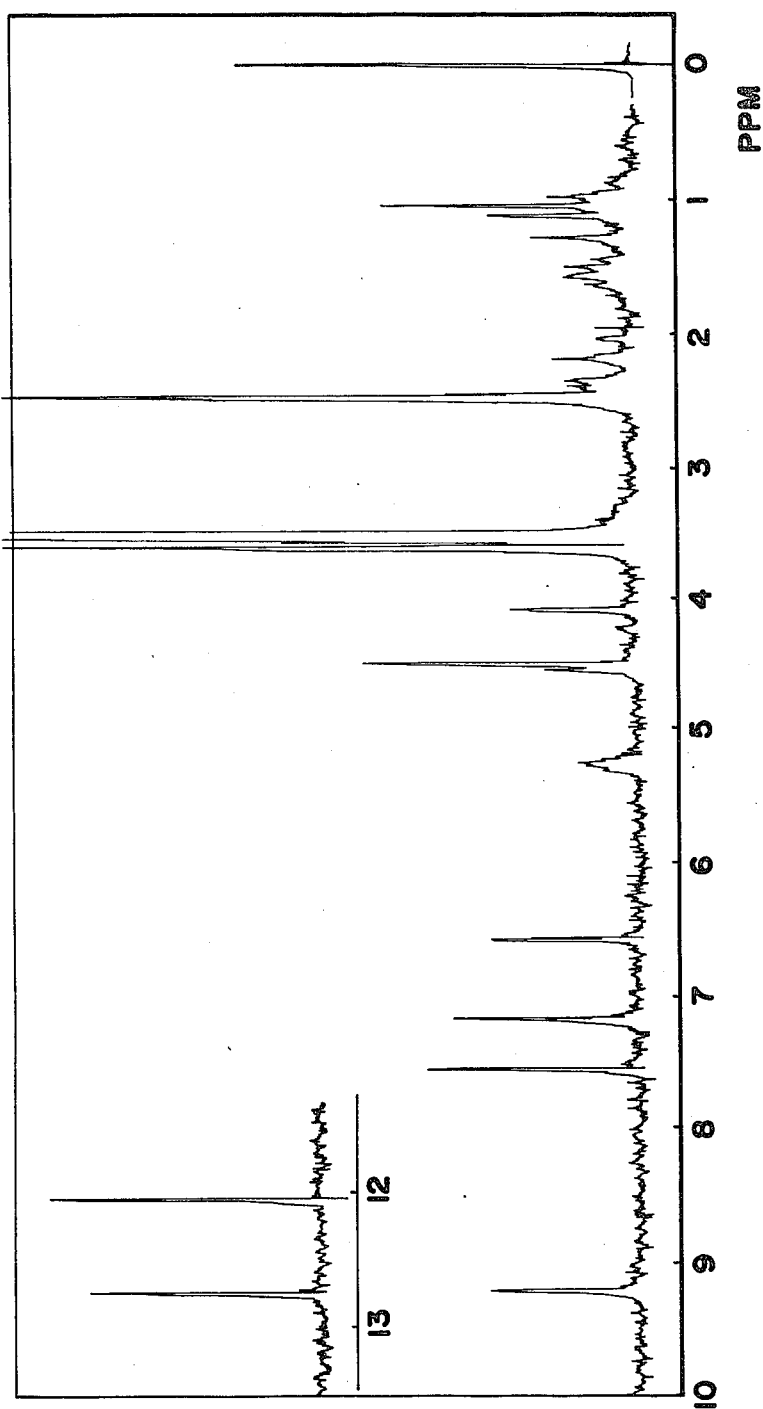
FIGS. 1 and 2 show the PMR spectra in $CDCl_3$ of 2-hydroxyaklavinone and 2-hydroxyaclacinomycin A, respectively.

The present invention provides the novel anthracycline compounds; 2-hydroxyaklavinone and 2-hydroxyaclacinomycin A, of the general formula I:

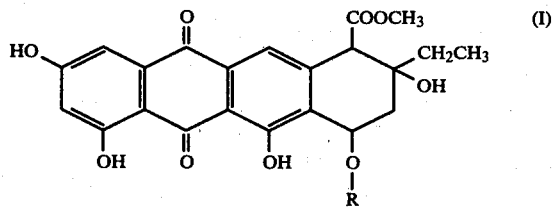

wherein R represents a hydrogen atom or the following sugar chain: rhodosamine-2-deoxyfucose-cinerulose residue

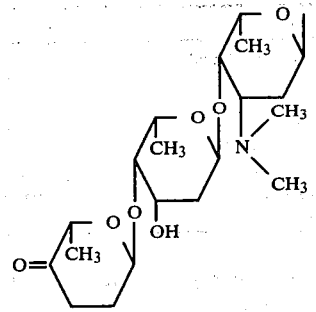

respectively, and the non-toxic acid addition salts thereof, and to a process for producing thereof. More particularly, the present invention relates to a novel antitumor anthracycline antibiotic 2-hydroxyaclacinomycin A having the general formula III:

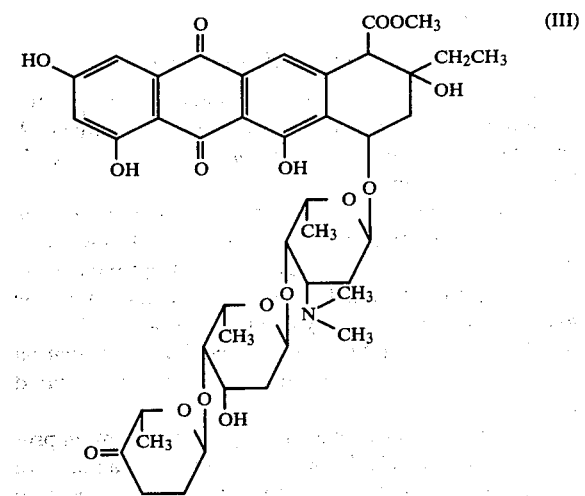

and the non-toxic acid addition salts thereof, and to a novel anthracycline compound, which is useful as precursor for producing 2-hydroxyaclacinomycin A, having the general formula II:

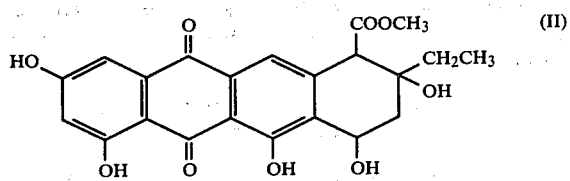

and to a microbiological process for the production thereof.

2-Hydroxyaclacinomycin A having the general formula III, in the present invention, can be favorably used as an anticancer agent owing to its potent antitumor activity against murine leukemia L 1210 and various experimental tumors with low toxicity. 2-Hydroxyaklavinone is an important and indispensable precursor for producing 2-hydroxyaclacinomycin A.

The present inventors have extensively studied the biosynthesis of anthracyclines and the microbial conversion of various anthracyclinones to produce more useful anthracycline antibiotics having more potent anticancer activity with lower toxicity than adriamycin and daunomycin which are widely used as anticancer agents, and have found that biosynthesis of anthracyclines can be controlled by two kinds of genes which independently synthesize their sugar and aglycone moieties. Thus various mutants may be obtained which lack capability of biosynthesizing the aglycone moiety and/or the sugar moiety.

Accordingly, a mutant lacking in capability of synthesizing aglycone moiety can not produce anthracycline glycosides, but could still produce biologically active antibiotics by exogenous addition of a proper anthracyclinone into the cultured medium. Thus, the inventors first established that a biologically inactive anthracyclinone aglycone is converted to new biologically active anthracycline antibiotics by use of such microorganisms. A new process for producing new rhodomycin-group of antibiotics has been filed as U.S. patent application Ser. No. 164,756 on June 30, 1980.

In the course of the study mentioned above, the present inventors have discovered a process for extensively producing 2-hydroxyaklavinone in a cultured medium and have discovered a process for producing a new potent antitumor anthracycline antibiotic 2-hydroxyaclacinomycin A by microbial conversion of 2-hydroxyaklavinone.

At present a process for producing 2-hydroxyaklavinone in the present invention is as follows.

Microorganisms used for the present invention are aclacinomycin-producing strains such as Streptomyces galilaeus MA144-M1 (FERM-P 2455, ATCC 31133) and various mutants therefrom obtained by UV treatment and mutation using chemical mutagens such as NTG (N-methyl-N'-nitro-N-nitrosoguanidine). Among them, for example, mutant strain Streptomyces galilaeus MA144-M1 ANR-58 is most preferably used for the present invention. This mutant ANR-58 was deposited in the American Type Culture Collection, 12301 Parklawn Drive, Rockville, Maryland 20852, U.S.A. and in the Fermentation Research Institute, Japan, and added to their permanent collections of microorganisms as ATCC 31671 and FERM-P 5081, respectively. The taxonomical properties of MA144-M1 ANR-58 were compared with those of the parent strain, Streptomyces galilaeus MA144-M1 as follows.

1. Morphology

There is no difference in morphological characteristics between both strains.

The vegetative hyphae (about 1μ in diameter) produced monopodial branched mycelium. Aerial mycelia at maturity formed open coiled chains composed of more than 10 spores. The spore shape was ellipsoidal (0.4–0.8×0.8–1.6μ in size), and its surface is smooth. They could not produce any sporophore in verticls, sporangium and sclerotium.

2. Properties on Various Media

The descriptions in the boxes follow the color standards of the "Color Harmony Manual" published by Container Corporation of America, U.S.A. and of "Japan Color Institute".

| Media | Parent strain MA144-M1 | Mutant strain ANR-58 |
|---|---|---|
| (1) Sucrose-nitrate agar (27° C.) | Growth: Colorless to pale yellowish brown (3gc); no aerial mycelium; no soluble pigment. | Growth: Colorless to pale yellow (1ba); no aerial mycelium; no soluble pigment. |

-continued

| Media | Parent strain MA144-M1 | Mutant strain ANR-58 |
|---|---|---|
| (2) Glucose-aspargine agar (27° C.) | Growth: Pale yellowish brown (3gc) to dull yellowish green (24lg); no aerial mycelium; no soluble pigment. | Growth: Dull yellow to light brown (4ie) to light reddish brown (5gc); light gray (d) aerial mycelium is slightly observed; pink to reddish brown soluble pigment. |
| (3) Glycerol-aspargine agar (ISP medium No. 5, 27° C.) | Growth: Yellowish orange (4ic) to brown (5lg); white to medium gray (2fe) aerial mycelium; brownish soluble pigment. | Growth: Grayish yellow (3ec) to moderate yellowish pink (4gc); no aerial mycelium; no soluble pigment. |
| (4) Inorganic salts-starch agar (ISP medium No. 4, 27° C.) | Growth: Pale orange (3ea) to pale yellowish brown (3ie); medium gray (2fe to e) aerial mycelium; brownish soluble pigment. | Growth: Pale yellow (2db); light gray (d) to light brownish gray (3fe) aerial mycelium; no soluble pigment or occasional brownish soluble pigment is slightly observed. |
| (5) Tyrosine agar (ISP medium No. 7, 27° C.) | Growth: Brownish gray (3li to 4li); white aerial mycelium; black soluble pigment. | Growth: Light grayish yellowish brown (3ge) to light grayish brown (4ig); no aerial mycelium; brown soluble pigment. |
| (6) Nutrient agar (27° C.) | Growth: Colorless to grayish brown; no aerial mycelium; brown soluble pigment. | Growth: Pale yellow (2db) to grayish yellow (3ec); light gray (d) aerial mycelium; brownish soluble pigment. |
| (7) Yeast extract malt agar (ISP medium No. 2, 27° C.) | Growth: Light brown (4lc) to brown (4ng); light gray (3fc) aerial mycelium; brown soluble pigment. | Growth: Light grayish reddish brown (4ge) to light brown (4ie); light brownish gray (3fe) aerial mycelium; light reddish brown (5gc) soluble pigment. |
| (8) Oatmeal agar (ISP medium No. 3, 27° C.) | Growth: Colorless to pale yellowish brown (2gc); medium gray (3fe) aerial mycelium; brown soluble pigment. | Growth: Pale yellow (2db); light gray (d) to yellowish gray (2dc) aerial mycelium; pink to reddish brown soluble pigment. |

3. Physiological Properties

Physiological characteristics such as gelatin liquefaction, starch hydrolysis, melanin formation, peptonization of skimmed milk and utilization of carbohydrates of the mutant strain ANR-58 are similar to those of the parent strain, as follows.

(1) Growth temperature was examined on maltose-yeast extract agar (maltose 1% w/v, yeast extract 0.4% w/v, available from Oriental Yeast Co., Tokyo, agar 3.5% w/v, pH 6.0) at 20, 24, 27, 30, 37 and 50° C. Optimal temperature range for growth found at 27° to 37° C., but no growth at 50° C.

(2) Gelatin liquefaction was examined (15% w/v gelatin medium, incubated at 20° C.; glucose-peptone-gelatin agar medium, incubated at 27° C.). Simple gelatin medium was weakly liquefied at 14 days incubation, but glucose-peptone-gelatin agar was weakly or moderately liquefied after 7 days incubation.

(3) Starch hydrolysis was examined on inorganic salts starch agar at 27° C. Weak hydrolysis was found after 5 days incubation.

(4) Coagulation and peptonization of skimmed milk was examined at 37° C. Skimmed milk was moderately to strongly peptonized after 5 days incubation and completely peptonized after about 17 days, but not coagulated.

(5) Melanin formation was examined in tryptone-yeast extract broth (ISP medium No. 1), peptone-yeast extraction agar (ISP medium No. 6) and tyrosine agar (ISP medium No. 7), incubated at 27° C. The formation of melanoid pigment was observed in all media.

(6) Utilization of carbon sources was examined on Pridham-Gottlieb basal medium (ISP medium No. 9) incubated at 27° C. Abundant growth was found with L-arabinose, D-xylose, glucose, D-fructose, sucrose, inositol, L-rhamnose, raffinose, but no growth with D-mannitol.

(7) Liquefaction of calcium malate was examined on calcium malate agar at 27° C. Calcium malate was liquefied.

(8) Nitrate reduction was examined on peptone medium containing 1% sodium nitrate (ISP medium No. 8), incubated at 27° C. The results were positive.

Strain MA144-M1 having the above characteristics has corresponded very closely with *Streptomyces galilaeus* ISP 5481 in morphology and color of the growth and mycelium on various media and physiological properties, and thus has been identified as *S. galilaeus* MA144-M1 (FERM-P 2455).

Various mutants used for the present invention can be obtained from said *Streptomyces galilaeus* MA144-M1 by the physical irradiation treatment such as α-, β-, γ- and X-ray irradiations, or by mutation using chemical mutagens such as NTG and diepoxybutane. As an example of obtaining a mutant strain, the NTG treatment, isolation and development of the mutant strain in the present invention can be carried out as follows.

(1) Mutation

Mutant strain ANR-58 was obtained from *Streptomyces galilaeus* MA144-M1 (ATCC 31133, FERM-P 2455) by the following procedure.

Spores were scratched from a YS (yeast extract and soluble starch) agar slant (yeast extract 0.3%, soluble starch 1.0%, agar 1.5%, pH 7.0) of *Streptomyces galilaeus* MA144-M1, grown for 1 week at 28° C., suspended in 5 ml of 0.2 M Tris-malate buffer (pH 7.5), and sonicated twice for 15 sec. (Ultra sonic distruptor, Model 1 UR-200P, 20 KHz, Tomy Seiko KK, Japan). The spore sonicate was filtered through sterile absorbent cotton filter tube (2 cm thick×0.8 cm in diameter). The resulting spore suspension (4 ml, about $5 \times 10^8$ spores/ml) was added to an ethanol solution of N-methyl-N'-nitro-N-nitrosoguanidine (NTG 10 mg/ml) at a concentration of 1 mg/ml and shaken at 30° C. for 60 min. in the dark. The killing rate was 90.6%. After centrifugation of the NTG-treated spore suspension at 3000 rpm for 10 min., the spores were resuspended in 0.85% physiological saline, diluted, inoculated onto YS agar plate and cultivated for 5 days at 28° C. to grow colonies.

(2) Isolation of Mutants

Colonies grown as above on YS agar plate were inoculated onto several YS agar slants and cultivated for one week at 28° C. An inoculum obtained from each slant by a platinum loop was inoculated in 4 ml of seed medium, and shake-cultured for 2 days at 28° C. Two ml of the seed culture were transferred to a 250-ml Erlenmeyer flask containing 25 ml of the sterilized production medium (as shown in Example 1), and cultivated for 2 days at 28° C. on a rotary shaker. Three ml of the cultured medium were taken, added to 0.5 ml of 0.1 M Tris-HCl buffer (pH 7.5) and 0.3 ml of toluene, mixed and extracted. Ten μl of toluene layer obtained by centrifugation were spotted onto silica gel thin-layer (Merck Co., $F_{254}$) and developed with chloroform-methanol (20:1) mixture. Among the colonies producing different aglycone from aklavinone, 2-hydroxyaklavinone-producing mutant ANR-58 was selected.

The following procedure is provided as an example for fermentation and isolation of 2-hydroxyaklavinone in the present invention:

ANR-58 culture grown on YS agar slant and stored at 6° to 7° C. was inoculated in a liquid medium, for example, of starch, glucose, organic nitrogent sources, and inorganic salts, and shake-cultured for 1 to 2 days at 25° to 32° C. to prepare the seed culture. Then, the seed culture is inoculated into a conventional liquid medium, for example, of sucrose, glucose, soybean meal, inorganic salts with 1 to 3% w/w, and aerobically cultivated at 25° to 32° C. for 36 to 100 hours.

Cultured medium thus obtained is centrifuged to separate mycelium from filtrate, and pigments are extracted from both mycelium and filtrate. Butanol, methanol and acidic buffer solution can be used to extract 2-hydroxyaklavinone from mycelium acetone, and chloroform, toluene and ethylacetate are favorably used for extraction from filtrate. Purification can be favorably performed by adsorption column and thin-layer chromatography using silicic acid (Wakogel C-200, Wako-Junyaku KK; Kieselgel 60 $PF_{254}$, Merck Co.), and gel filtration using Sephadex LH-20 (Cross-linked dextran gels, Pharmacia Fine Chemical AB).

Chemical structure of the compound thus obtained in the present invention was determined by ultraviolet and visible absorption (UV), infrared absorption (IR), 100 MHz proton NMR and mass spectral analyses, and the compound was identified as 2-hydroxyaklavinone which has physical-chemical properties as shown in Example 1.

A process for producing and isolating an anthracycline glycoside 2-hydroxyaclacinomycin A in the present invention from the anthracyclinone 2-hydroxyaklavinone obtained above, is as follows.

An aclacinomycin-producing strain (Japan P-54-3809, J. Antibiotics 28, 830, 834, 1975, ibid. 32, 791–800, 801–819, 1979) such as *Streptomyces galilaeus* MA144-M1 (ATCC 31133) and various mutants therefrom, for example strain KE 303 (FERM-P 4808), ATCC No. 31649, which can not produce anthracycline pigments and are capable of converting exogenous anthracyclinone to anthracycline glycosides can be preferably used for the present invention. The general procedure for obtaining mutant strains from *Streptomyces galilaeus* MA144-M1 which are incapable of producing pigments (anthracycline antibiotics) and are capable of converting anthracyclinone to anthracycline glycosides is described in the following example.

(1) Mutation Procedure

Anthracycline pigment non-producing mutant KE 303, for example, can be obtained from the parent strain, *Streptomyces galilaeus* MA144-M1 by the NTG treatment as follows.

The spores were scratched from a YS agar slant (yeast extract 0.3%, soluble starch 1.0%, agar 1.5%, pH 7.0) of *S. galilaeus* MA 144-M1, grown for 1 week at 28° C., suspended in 5 ml of 0.2 M Tris-malate buffer (pH 7.5), and sonicated twice for 15 sec. (Ultra sonic distruptor, Model 1UR-200P, 20 KHz, Tomy Seiko KK, Japan). The spore sonicate was filtered through a sterile absorbent cotton filter tube (2 cm thick×0.8 cm in diameter), and the resulting spore suspension (4 ml, about $5 \times 10^8$ spores/ml) was added to an ethanol solution of N-methyl-N'-nitro-N-nitrosoguanidine (NTG, 10 mg/ml) at a concentration of 1 mg/ml and shaken at 30° C. for 60 min. in the dark. The killing rate is generally 75 to 80%. After centrifugation of the spore suspension for 10 min. at 300 rpm, the spores were resuspended in 0.85% of physiological saline, diluted, inoculated onto YS agar plate and cultivated for 5 days at 28° C. to grow colonies.

(2) Isolation of Mutants

Colonies grown as above on YS agar plate were inoculated to YS agar slant and cultivated for 1 week at 28° C. An inoculum obtained from each slant by a platinum loop was inoculated in 4 ml of seed medium (yeast extract 1%, soluble starch 1%, pH 7.0), shake-cultured for 2 days at 28° C. Two ml of the seed culture were transferred to a 250-ml Erlenmeyer flask containing 25 ml of sterilized production medium (glucose 1%, soluble starch 1.5%, yeast extract 0.1%, soybean meal 3%, $K_2HPO_4$ 0.1%, $MgSO_4.7H_2O$ 0.1%, NaCl 0.3%, mineral 0.125%, pH 7.4), and cultivated for 2 days at 28° C. on a rotary shaker. Five ml of the cultured medium were centrifuged, and yellow pigment having absorbance of aklavinone at 430 nm was extracted from mycelium with 5 ml of acetone and determined by a spectrophotometer. Thus, anthracycline non-producing colonies were selected. Then, capability of producing anthracycline glycosides from the exogenously added anthracyclinones into the culture medium was examined in every anthracycline non-producing colony. An inoculum of a pigment non-producing mutant strain was inoculated in the above seed medium, which was then shake-cultured at 28° C. for 2 days. 2.5 ml of seed culture was transferred into a 250-ml Erlenmeyer flask containing 25 ml of the above production medium, cultivated for 20 hours at 28° C. on a rotary shaker, and then 0.5 ml of aklavinone solution was added (1 mg/ml im methanol, final concentration: 20 μg/ml). After 24 more hours of cultivation, 5 ml of the culture were centrifuged, and the mycelium was extracted with 5 ml of acetone. After concentrating the acetone layer under reduced pressure, 0.1 ml of toluene and 1 ml of 0.2 M Tris-HCl buffer (pH 7.5) were added to the concentrate, dissolved and the toluene layer was obtained for analysis. Twenty to 50 μl of the toluene layer were spotted onto silica gel thin-layer ($F_{254}$, E. Merck Co.) together with authentic aclacinomycin A, and developed with a mixture of chloroform-methanol (20:1). Thus, the mutant strains possessing ability to produce aclacinomycin A can be used for the present invention.

According to the above method, at first anthracycline non-producing mutants were isolated, and then among them, a mutant capable of producing anthracycline glycosides from the exogenous-added anthracyclinone as substrate by connecting sugar residue formed in the culture medium can be selected. In the present invention, other anthracycline-producing microorganisms such as *Streptomyces galilaeus* ATCC 14969, *S. cinereoruber* ATCC 19740, *S. antibioticus* ATCC 8663, *S. nivereoruber* ATCC 14971, which can produce various anthracycline glycosides such as cinerubin, galerubin and pyrromycin having the same sugar moiety as aclacinomycin A, also can be used for isolating mutants.

The substrate, 2-hydroxyaklavinone, obtained according to the above-mentioned methods, can be used not only in pure form but in crude preparation, for example as the methanol solution of crude concentrate containing 2-hydroxyaklavinone extracted with acetone from the ANR-58 culture medium in the present invention.

Production of the compound in the present invention is carried out as follows. The said strain, for example KE 303 capable of converting exogenous anthracyclinones to anthracycline glycosides, is grown on an agar slant (0.3% yeast extract, 1% soluble starch, 1.5% agar, pH 7.2), stored at 6° to 7° C., and shake-cultured for 1 to 3 days at 25° to 32° C. in a conventional liquid medium of starch, glucose, organic nitrogen sources, and inorganic salts to prepare the seed culture. Then, the seed culture is inoculated into a conventional liquid medium, for example, of sucrose, glucose, soybean meal and inorganic salts with 1 to 3% in volume, and shake-cultured at 25° to 32° C. for 15 to 48 hours. During cultivation, methanol solution of 2-hydroxyaklavinone is added to the cultured medium at the final concentration of 10 to 200 μg/ml on the logarithmic phase of microbial growth, and cultivation is further continued for 15 to 72 hours to complete the microbial conversion. During the fermentation, defoamer such as Adecanol (Asahi Denka Ind. Co., commercial name) and silicone (Shinetsu Chem. Ind. Co.) can be used for preventing foaming. Cultured medium thus obtained is centrifuged to separate mycelium from filtrate, and crude pigments containing the compound in the present invention are extracted and purified from both mycelium and filtrate as follows.

To extract the compound of the present invention, acetone, methanol, chloroform, ethyl acetate, toluene, dilute mineral acid and acidic buffer solution can be used. Purification can be favorably carried out by column and thin-layer chromatography using Sephadex LH-20 (Pharmacia Fine Chem. Co.), silica gel (Merck Co., or Wako Junyaku Co.) and CM-cellulose, high-performance liquid chromatography, counter current distribution and any combination of these techniques. For example, the compound in the present invention can be separated from crude pigments and the residual anthracycline aglycone used as substrate by gel filtration using Sephadex LH-20, and easily purified by the repeated preparative silica gel thin-layer chromatography (PF$_{254}$, Merck Co.) using various solvent systems. Chemical structure of the compound thus obtained in the present invention was determined by ultraviolet and visible absorption (UV), infrared absorption (IR), 100 MHz proton and $^{13}$C-NMR and mass spectral analyses, and also by spectral analyses and Rf values on thin-layer of the aglycone and sugar moieties obtained by acid hydrolysis. Determination of sugar chain and its connecting position to aglycone was performed according to the methods used for the structural analysis of aclacinomycin A. The compound in the present invention has the same trisaccharide chain consisting of L-rhodosamine-2-deoxy-L-fucose-L-cinerulose as in aclacinomycin A (J. Antibiotics 32, 801–819, 1979) at the C-7 position of 2-hydroxyaklavinone used as substrate for microbial conversion, and thus the compound is identified as 2-hydroxyaclacinomycin A.

The compounds in the present invention can be obtained as free base or non-toxic acid addition salts with a variety of organic and inorganic salt-forming reagents. Thus, acid addition salt can be formed with such acids as sulfuric, phosphoric, hydrochloric, bromic, nitric, acetic, propionic, maleic, oleic, citric, succinic, tartaric, fumaric, glutamic, pantothenic, laurylsulfonic, methanesulfonic, naphtalenesulfonic and related acids. For the purpose as a cancer chemotherapeutic agent, the free base form of the compounds is equivalent to their non-toxic acid addition salts. The free base of the compounds can be lyophilized with non-toxic acid in the proper solution or acid addition salts can be recovered by precipitation from solvents capable of slightly dissolving their non-toxic acid addition salts. These acid addition salts can be changed into original free base form by neutralizing with basic compounds, and vice versa.

The following are physical-chemical properties of 2-hydroxyaclacinomycin A in the present invention:

Appearance: Yellowish brown powder
Melting point: 165–167° C.
Molecular weight: 827.9
Elementary analysis: C$_{42}$H$_{53}$NO$_{16}$

|   | Calcd. (%) | Found (%) |
|---|---|---|
| C | 60.93 | 60.27 |
| H | 6.45 | 6.20 |
| N | 1.69 | 1.64 |
| O | 30.93 | — |

Figure 2:
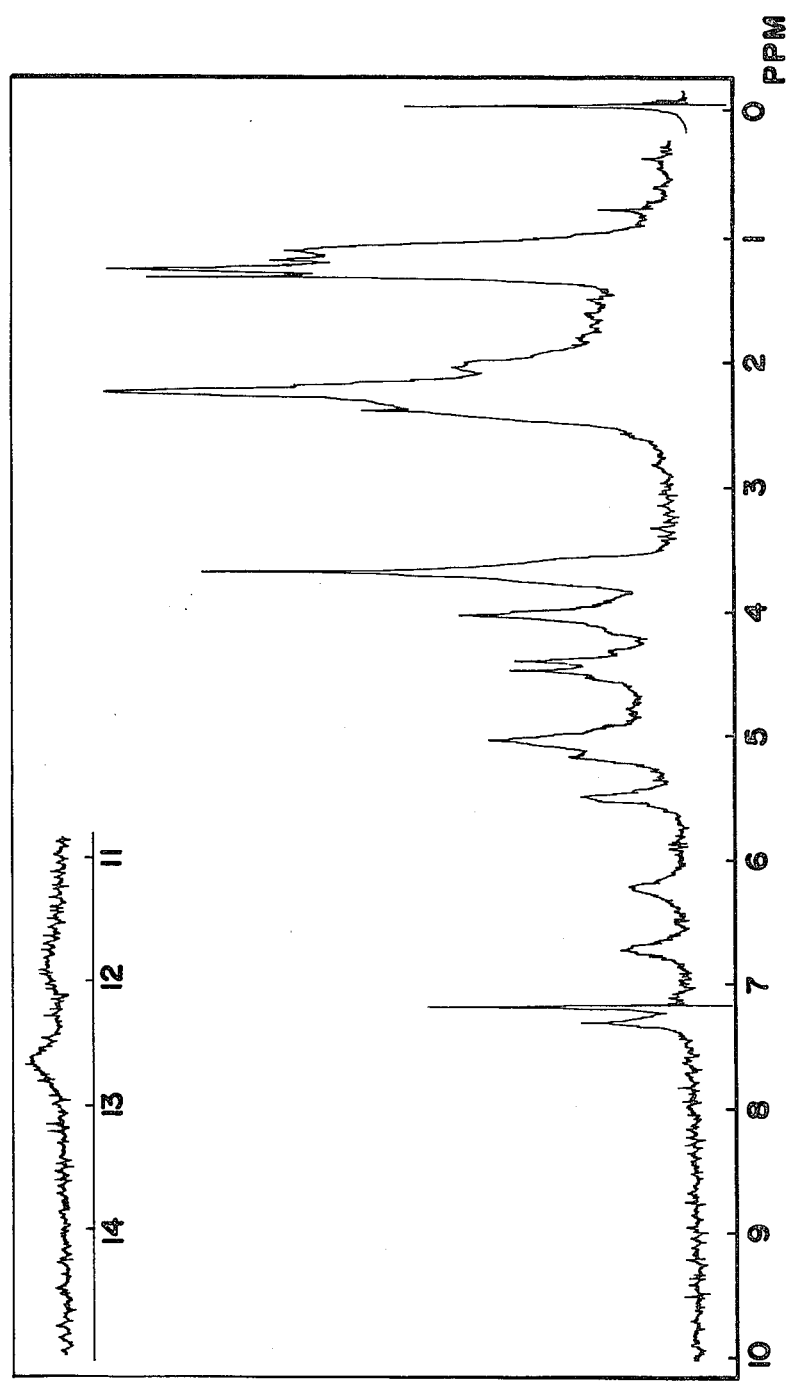

$[\alpha]_D^{23}$: +42.3° (C 0.04, MeOH)
UV and visible absorption spectrum:
$\lambda_{max}^{90\% MeOH}$ nm(E$_{1cm}^{1\%}$): 222(375), 256(235), 295(207), 450(110)
$\lambda_{max}^{0.1N HCl-90\% MeOH}$ nm(E$_{1cm}^{1\%}$): 226(448), 254(238), 268(245), 291(251), 440(158)
$\lambda_{max}^{0.1N NaOH-90\% MeOH}$ nm(E$_{1cm}^{1\%}$): 240s(370), 297(252), 330s(196), 540(143)
IR (KBr), cm$^{-1}$: 3450, 2975, 2940, 1735, 1675, 1620, 1610, 1450, 1400, 1380, 1300, 1255, 1230, 1170, 1120, 1010
PMR spectrum (100 MHz, CDCl$_3$), δppm: (FIG. 2)

The following describes the usefulness of the compound in the present invention.

The compound in the present invention inhibited markedly the growth and nucleic acid biosynthesis of murine leukemia L 1210 cells in culture. In an example, L 1210 cells were inoculated in RPMI (Rosewell Park Memorial Institute) 1640 medium containing 20% calf serum at the cell density of 5×10$^4$ cells/ml, and the compound in the present invention was simultaneously added to the medium at the concentration of 0.1 and 0.5 μg/ml and incubated at 37° C. in a CO$_2$ incubator. 50% growth inhibition concentration of the compound over controls was determined. L 1210 cells as described above were also inoculated at 5×10$^5$ cells in RPMI 1640 medium containing 10% calf serum and incubated at 37° C. for 1 to 2 hours in a CO$_2$ incubator. The cells were cultured for 15 min. at 37° C. after the compound of the present invention was added at various concentrations, and then $^{14}$C-uridine (0.05 μCi/ml) or $^{14}$C-thymidine (0.05 μCi/ml) was added and incubated for 60 additional min. at 37° C. After stopping the pulse-labeling by addition of 10% trichloroacetic acid (TCA) solution to the reaction mixture, acid-insoluble materials were precipitated, washed three times with 5 to 10% TCA, and dissolved in a small amount of formic acid. Then, radioactivity was determined, and inhibitory effects on the RNA and DNA biosynthesis were indicated by the 50% inhibition concentration (IC$_{50}$) of the incorporation of radioactivity over controls.

Antitumor effect against experimental animal tumor was examined as follows. $CDF_1$ mice were inoculated with $1\times 10^5$ cells of L 1210 cells intraperitoneally, and 2-hydroxyaclacinomycin A was administered intraperitoneally once daily for 10 days consecutively, 24 hours after inoculation. Prolongation of lifespan over controls (injected with only physiological saline instead of 2-hydroxyaclacinomycin A) is shown in Table 1. $LD_{50}$ value in dd mice is also shown in Table 1 comparing with that of aclacinomycin A.

TABLE 1

Antitumor activity and acute toxicity of 2-hydroxyaclacinomycin A and aclacinomycin A

| Test | 2-Hydroxyaclacinomycin A | Aclacinomycin A |
|---|---|---|
| 1. in vivo antitumor activity: L 1210 (mg/kg/day) | T/C* (%) | |
| 12 | 127 | — |
| 8 | 194 | Toxic |
| 6 | 218 | 105 |
| 4 | 201 | 205 |
| 2 | 176 | 165 |
| 1 | 153 | 146 |
| 0.5 | 145 | 130 |
| 2. in vitro activity: L 1210 | $IC_{50}$ (μg/ml) | |
| Growth | 0.10 | 0.12 |
| DNA synthesis | 0.95 | 1.10 |
| RNA synthesis | 0.10 | 0.10 |
| 3. Toxicity ($LD_{50}$: mg/kg) dd mice, i.p. | 50.0 | 22.6 |

*"T/C" is % of prolongation of lifespan over controls (T: treated, C: control).

From these results, 2-hydroxyaclacinomycin A in the present invention suppressed the growth of murine leukemic cells at low concentration and exhibited marked prolongation of lifespan of L 1210-bearing mice. Furthermore its acute toxicity was much more less than those of known anthracycline antibiotics such as daunomycin and adriamycin. Comparing with aclacinomycin A which is one of the least toxic and the least cardiotoxic anthracycline antibiotics, 2-hydroxyaclacinomycin A has more potent antitumor activity with broader effective dose range (about a twice wider range of effective dose than that of aclacinomycin A) and less cardiotoxicity.

Moreover, 2-hydroxyaclacinomycin A specifically inhibited RNA synthesis with similar mode of action to aclacinomycin and rhodomycin-group of antibiotics.

The following examples are provided for illustrative purpose only and are not intended to limit the scope of the invention.

EXAMPLE 1

Process for producing 2-hydroxyaklavinone

A nutrient medium having the following composition was prepared:
Soluble starch: 1.0%
Glucose: 1.0%
Soybean meal (Meat, Ajinomoto Co., Inc.): 1.0%
$K_2HPO_4$: 0.1%
$MgSO_4.7H_2O$: 0.1%
$CuSO_4.5H_2O$: 0.0007%
$FeSO_4.7H_2O$: 0.0001%
$MnCl_2.4H_2O$: 0.0008%
$ZnSO_4.7H_2O$: 0.0002%
pH: 7.4

One hundred ml of this medium was sterilized in a 500-ml Erlenmeyer flask which was inoculated respectively from an agar slant culture of *Streptomyces galilaeus* MA144-M1 ANR-58 (FERM-P 5081) by platinum loop, and shake-cultured for 48 hours at 28° C. to prepare the seed culture. Three hundreds 500-ml Erlenmeyer flasks containing 50 ml of a previously sterilized production medium consisting of glucose 1%, meat (soybean meal, Ajinomoto Co., Inc.) 3%, $K_2HPO_4$ 0.1%, $MgSO_4.7H_2O$ 0.1%, $CuSO_4.5H_2O$ 0.0007%, $FeSO_4.7H_2O$ 0.0001%, $MnCl_2.4H_2O$ 0.0008%, $ZnSO_4.7H_2O$ 0.0002%, pH 7.4 were inoculated with 1 ml of the above seed culture, and cultivated for 48 hours at 28° C. on a rotary shaker (220 rpm). Fourteen liters of the cultured medium was centrifuged to harvest the mycelium, and the product was extracted with 2.5 liters of acetone. After concentrating the acetone extract under reduced pressure, the pigment was reextracted with 1 liter of chloroform and the chloroform layer was concentrated to obtain 1.8 g of oily substance. The oily substance was dissolved in 30 ml of chloroform, applied to silica gel column (30 cm high×3.5 cm in diameter) and eluted with chloroform-methanol (50:1) mixture. Initial yellow fractions were collected, concentrated to dryness (180 mg), dissolved in ethylacetate, spotted onto silica gel preparative thin-layer ($F_{254}$, Merck Co.), and developed with chloroform-methanol (30:1) mixture. Main band corresponding to Rf 0.77 was scratched off, eluted with ethylacetate, concentrated to dryness, and crystalized in acetone-n-hexane. The resulting yellow needle was 218 mg, and had the following properties.

Crystal: Orange yellow to yellow needle
Melting point: 183-185° C. (decomposition)
Elementary analysis: $C_{22}H_{20}O_9$

| | C | H | O |
|---|---|---|---|
| Calcd. (%) | 61.68 | 4.71 | 33.61 |
| Found (%) | 61.22 | 4.82 | 33.96 |

Molecular weight (m/e): 428 (Mass spectral analysis)
UV and visible absorption spectrum:

| | 90% MeOH | 0.1N HCl-90% MeOH | 0.1N NaOH-90% MeOH |
|---|---|---|---|
| $\lambda_{max}^{nm}$ ($E_{1cm}^{1\%}$) | 224(692) | 225(755) | 235s(760) |
| | 256(448) | 254(413) | 260s(370) |
| | 270s(400) | 269(448) | 298s(495) |
| | 290(404) | 290(450) | 310(508) |
| | 440(240) | 440(281) | 530(273) |

IR spectrum (KBr): 3520, 3450, 1730, 1680, 1620, 1280, 1250, 1030 $cm^{-1}$
NMR (100 MHz, $CDCl_3$: $CD_3OD$ = 1:1): FIG. 1

EXAMPLE 2

A nutrient medium having the following composition was prepared:
Soluble starch: 1.5%
Glucose: 1.0%
Soybean meal: 1.0%
$K_2HPO_4$: 0.1%
$MgSO_4.7H_2O$: 0.1%
$CuSO_4.5H_2O$: 0.0007%
$FeSO_4.7H_2O$: 0.0001%
$MnCl_2.4H_2O$: 0.0008%
$ZnSO_4.7H_2O$: 0.0002%
pH: 7.4

One hundred ml o this medium was sterilized in a 500-ml Erlenmeyer flask which was inoculated from an agar slant culture of *Streptomyces galilaeus* KE 303 ATCC No. 31649 by platinum loop, and incubated for 48 hours at 28° C. on a rotary shaker to prepare the seed culture. One thousand 500-ml flasks containing 50 ml of the previously sterilized medium of the same composition as above except increasing soybean meal and yeast extract to 2% and 0.2%, respectively, were inoculated with 1 ml of the seed culture, cultivated for 17 hours at 28° C. on a rotary shaker (210 rpm), and then 0.5 ml of 2-hydroxyaklavinone solution in methanol (2 mg/ml) was added to each flask at the final concentration of 20 μg/ml (total amount: 1 g). Cultivation was continued for 24 hours. To determine the production yield of 2-hydroxyaclacinomycin A, 5 ml of the cultured medium was extracted with chloroform-methanol (3:2) mixture, concentrated to dryness, dissolved in 0.2 ml of chloroform, spotted onto silica gel thin-layer (Merck Co., F$_{254}$ plate), and developed with chloroform-methanol-conc. ammonia (50:10:0.5) mixture. After drying, the thin-layer plate spots corresponding to 2-hydroxyaclacinomycin A having Rf value at 0.51 and residual 2-hydroxyaklavinone having Rf value at 0.30 were determined by Shimazu thin-layer chromatoscanner, Model CS-910. The conversion rate of 2-hydroxyaklavinone to 2-hydroxyaclacinomycin A was over 90% to yield 680 mg of the product. Fifty liters of the above cultured medium were centrifuged to harvest the mycelium, and the product was extracted from the mycelium with 8 liters of acetone, concentrated to one third volume, and reextracted with 3 liters of chloroform. The chloroform extract was concentrated to dryness to obtain crude product.

EXAMPLE 3

The crude product obtained in Example 2 was dissolved in 50 ml of methanol, centrifuged to remove insoluble materials, subjected to Sephadex LH-20 column (40×5.0 cm) and eluted with methanol.

Initial yellow fractions were collected, concentrated to dryness, dissolved in a small amount of chloroform, applied onto preparative silica gel thin-layer (50 plates of Kieselgel 60 PF$_{254}$, E. Merck Co.), and developed with chloroform-methanol-conc. ammonia (50:10:0.3) mixture. Main band containing 2-hydroxyaclacinomycin A having Rf value at 0.68 was scratched, extracted with 200 ml of chloroform-methanol (4:1) mixture, and washed with suitable amount of distilled water by shaking. The chloroform layer was concentrated to dryness, dissolved in a small amount of chloroform, applied onto the above-mentioned thin-layer (25 plates), and developed with chloroform-methanol-acetic acid (80:10:0.5) mixture. Main yellow band showing Rf 0.22 was scratched off, and extracted with 200 ml of chloroform-methanol-conc. ammonia (40:10:0.5) mixture. The chloroform layer was washed with water, and concentrated to dryness to obtain 388 mg of refined substance. This preparation was dissolved in 30 ml of methanol and passed through Sephadex LH-20 column (40×5 cm), and then the eluate was concentrated and dissolved in 20 ml of 0.2 M acetate buffer (pH 3.5). After removing a small amount of insoluble materials by centrifugation, the supernatant was neutralized with 4 N NaOH in ice bath and extracted with chloroform. The chloroform extract was washed successively with 0.01 M EDTA (pH 6.0) and water, dried over sodium bicarbonate and concentrated under reduced pressure. The concentrate was added by excess n-hexane to form orange precipitate, and 293 mg of pure 2-hydroxyaclacinomycin A were obtained by filtration and drying of the precipitate in vacuo.

What is claimed is:

1. 2-Hydroxyaklavinone and 2-hydroxyaclacinomycin A of the formula I:

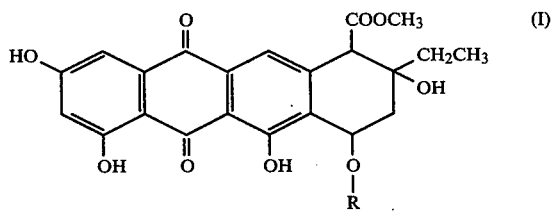

wherein R is selected from the group consisting of a hydrogen atom and a sugar residue: rhodosamine-2-deoxyfucose-cinerulose,

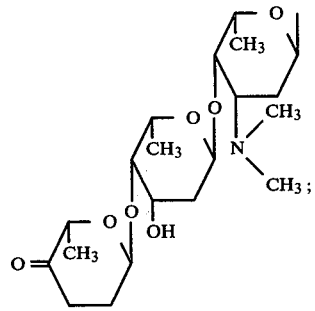

and the non-toxic acid addition salts thereof when R is the sugar residue.

2. The compound of claim 1, wherein R is rhodosamine-2-deoxyfucose-cinerulose and the non-toxic, acid addition salts thereof.

3. A compound of the formula I of claim 1 wherein R is hydrogen.

* * * * *